United States Patent [19]

Vick

[11] 4,086,631
[45] Apr. 25, 1978

[54] HEMATOCRIT MEASUREMENT IN AN AUTOMATIC HEMATOLOGY ANALYZER

[75] Inventor: Howard Andrew Vick, Pearland, Tex.

[73] Assignees: Hycel, Inc., Houston, Tex.; Hycel, Inc., Houston, Tex.

[21] Appl. No.: 752,015

[22] Filed: Dec. 20, 1976

Related U.S. Application Data

[62] Division of Ser. No. 535,495, Dec. 23, 1974, Pat. No. 4,052,596.

[51] Int. Cl.² ............... G01N 15/08; G06M 11/04
[52] U.S. Cl. ................... 364/416; 128/2 G; 235/92 PC; 364/555; 364/564
[58] Field of Search ........... 235/183, 151.3, 92 PC; 324/71 CP; 364/416; 328/127

[56] References Cited

U.S. PATENT DOCUMENTS

| | | | |
|---|---|---|---|
| 3,185,820 | 5/1965 | Williams et al. | 235/151.35 |
| 3,304,413 | 2/1967 | Lehman et al. | 235/151.3 |
| 3,812,425 | 5/1974 | Miller | 235/92 PC |
| 3,813,532 | 5/1974 | Sato et al. | 328/127 |
| 3,828,260 | 8/1974 | Underwood | 235/92 PC |
| 3,875,428 | 4/1975 | Le Blanc et al. | 328/127 |
| 3,973,194 | 8/1976 | McMorris et al. | 324/71 CP |

FOREIGN PATENT DOCUMENTS 1,548,794  9/1969  Germany ............... 328/127

Primary Examiner—Felix D. Gruber
Attorney, Agent, or Firm—Robert P. Cogan; Timothy L. Burgess; Robert P. Cogan

[57]        ABSTRACT

In a hematology analyzer, peaks of pulses indicative of red blood cells in a sample during a count are detected. Peak detecting means produce a gate signal connected to gate means which couple a portion of each pulse in the time vicinity of its peak to integration means. The level accumulated in the integration means is indicative of total cell volume, and hence indicative of hematocrit for a known sample volume.

5 Claims, 2 Drawing Figures

HEMATOCRIT MEASUREMENT IN AN AUTOMATIC HEMATOLOGY ANALYZER

This is a division of application Ser. No. 535,495 filed on Dec. 23, 1974 and now U.S. Pat. No. 4,052,596.

This invention relates to a hematology analyzer, and more particularly, to an improvement to such an analyzer for providing output information relating to the hematocrit, the mean corpuscular volume, the mean corpuscular hemoglobin and the mean corpuscular hemoglobin concentration of a blood sample, in addition to the already provided hemoglobin and red blood cell count information of that sample of blood.

The prior art includes apparatus offered for sale by Hycel, Inc. of Houston, Texas, known as the Hycel Counter 300, Model HC 300 which performs a red blood cell count, a white blood cell count and a hemoglobin content determination on a sample of blood. The red blood cell count may be made by preparing a solution of whole blood in a buffered electrolyte dilutant so that the blood is diluted, for instance, 160,000 times. A precise volume of this solution is then passed through a small opening of approximately 100 microns in diameter, and electrical apparatus connected to the opening monitors the impedance of the solution flowing therein. As a blood cell passes through the opening, the impedance increases causing a pulse to be provided by the electrical apparatus. The magnitude of this pulse is proportional to the size of the cell being measured, and the number of pulses equals the number of cells in the precise volume.

In the prior art apparatus, white blood cells are measured in substantially the same manner as described above for the red blood cells except that a chemical lycing agent is added to distroy the red blood cells and a larger volume of solution is measured, or on the other hand, a less diluted solution is measured. It should be noted that in the case where the red blood cells are being measured, approximately one or two percent of those detected cells will be white blood cells. Furthermore, the prior art apparatus measures the hemoglobin content of the blood by mixing a specific chemical with the blood and thereafter performing a colormetric determination in a known manner. The output of the photocell used in the colormetric determination is analog voltage in which the magnitude is proportional to the hemoglobin content.

In addition to the red blood cell count, the white blood cell count and the hemoglobin content value of the blood, a physician may desire to know the hematocrit value of the blood, the mean corpuscular volume of the blood, the mean corpuscular hemoglobin of the blood and the mean corpuscular hemoglobin concentration of the blood.

The hematocrit of the blood is the percent of the blood cell volume to the total amount of blood of the sample. The classical manner of determining the hematocrit is to add an anticoagulant to the blood sample and centrifuge it until the cells and serum are separated with the cells settling to the bottom and the serum on the top. Then a volume measurement of the cells and the serum is made and the percentage of the cells to the total is determined as a hematocrit value. A typical value of the mean corpuscular volume may be between 84 and 95 cubic microns.

The mean corpuscular hemoglobin is the amount of hemoglobin per red blood cell of the blood and may be determined by dividing ten times the hemoglobin in grams per liter by the number of red blood cells per cubic millimeter of blood and may be expressed in units of micro-micrograms. A typical value for the mean corpuscular hemoglobin would be 28 to 32 micromicrograms.

The mean corpuscular hemoglobin concentration is the amount of hemoglobin expressed as a percent of the volume of a red blood cell and may be calculated by dividing the hemoglobin by the hematocrit. The result is expressed in terms of percentage, with a typical value being in the range of 33–38%.

In order for the hematology analyzer to provide all the desired information to the physician, it should provide a red blood cell count, a white blood cell count, a hemoglobin value, a hematocrit value, a mean corpuscular volume value, a mean corpuscular hemoglobin value, and a mean corpuscular hemoglobin concentration value. The prior art device provides only the first three of these values. The red and white blood cell counts are made by applying the pulses provided when monitoring the impedance of the flow cell to a digital counter. After a precise volume passes through the flow cell, the count of the counter is provided to a digital display where it may be read by the operator. In the case of the hemoglobin, the analog voltage provided as a result of the hemoglobin colormetric determination is scaled and applied to the data input of an analog to digital converter and a direct current reference voltage is connected to the reference input. The digital output, is then provided to the digital display upon command of the operator.

In order to utilize the prior art device to provide the additional four values, it is necessary to determine the hematocrit value and provide dividing means to be able to divide the hematocrit and hemoglobin by the number of red blood cells and to divide the hemoglobin by the hematocrit.

U.S. Pat. No. 3,439,267, entitled "Automatic Hematocrit Measuring Apparatus" discloses apparatus for determining the hematocrit value in a diluted solution of whole blood, and the U.S. Pat. No. 3,473,010 entitled "Apparatus and Method for Determining Mean Particle Volume" discloses apparatus for determining the mean corpuscular volume of the blood. The apparatus disclosed by both of these patents must be used totally in addition to the prior art analyzer described above. It would be more desirable to provide apparatus which can use at least some existing part of the prior art apparatus, where possible, in order to reduce the cost involved in providing the additional four values.

In accordance with one preferred embodiment of this invention, there is provided a circuit for selectively providing a digital signal manifesting a ratio of selected ones of a plurality of analog signals comprising an analog-to-digital converter means having a data input, a reference input and a digital output. The digital output provides a digital signal manifesting a value relating to the analog signal applied to the data input divided by the analog signal applied to the reference input. In addition, there is provided switching means for connecting the selected analog signals to the data and reference inputs of the conversion means to provide the selected digital signals.

One preferred embodiment of this invention is described hereinafter with reference being made to the following FIGURES. in which.

Figure 1:
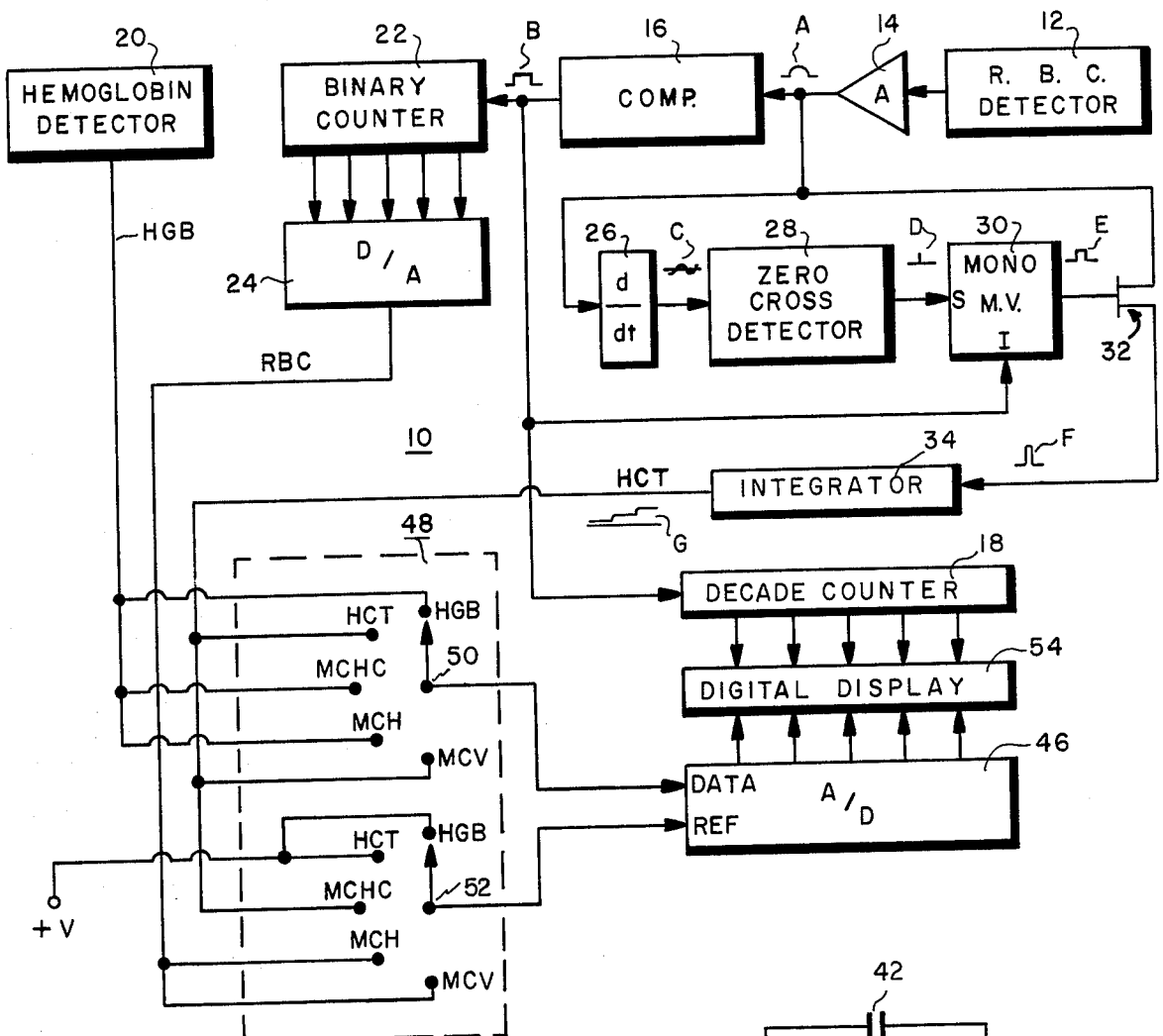
FIG. 1 shows a block diagram of the hematology analyzer for measuring seven hematological parameters of blood.

Referring now to FIG. 1, hematology analyzer 10 includes red blood cell detector 12 which provides a pulse signal to amplifier 14. Detector 12 may be a flow cell type apparatus, known in the prior art, in which a precise volume of diluted blood is allowed to flow through a small opening of, for instance, 100 microns in diameter and the impedance of that opening is constantly monitored. Each time a red blood cell enters the opening, the impedance changes, causing the output voltage applied through the blood in the opening to change amplitude. The amount of amplitude change depends upon the impedance in the flow cell and that impedance, in turn, depends upon the size of the red blood cell. Accordingly each time a blood cell is in the opening, a pulse signal is provided on the electrical line monitoring the impedance change. The duration of each pulse depends upon the time a blood cell is in the flow cell and this duration is variable, although typically about thirty micro-seconds.

Figure 2:
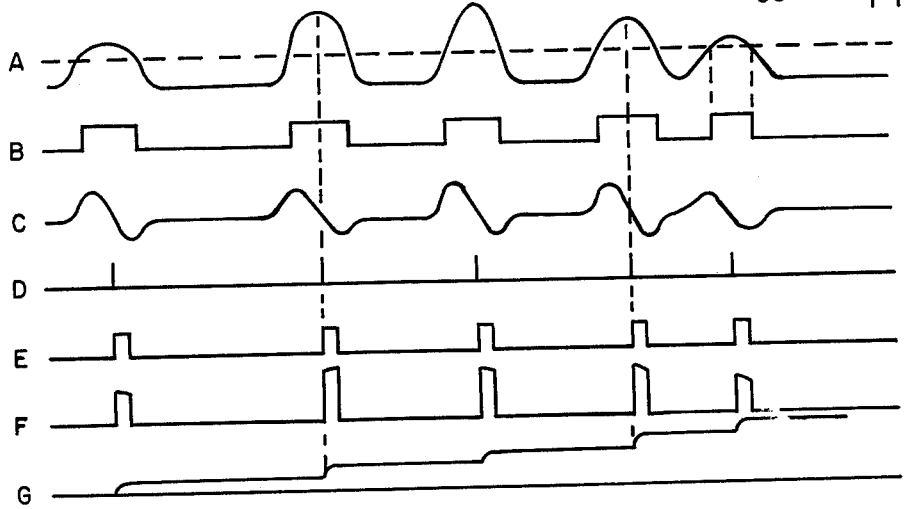
FIG. 2 shows a series of waveform signals useful in understanding the operation of the analyzer shown in FIG. 1.

After the voltage from detector 12 is amplified by amplifier 14, it appears as waveform A shown in FIG. 2. It should be noted that there is no periodic time cycle of occurrence of the pulses and they have differing amplitudes reflecting the different size cells.

Comparator 16 responds to waveform A by providing a pulse signal, which is substantially square shaped, as indicated by wave form B, during the time the amplitude of the waveform A exceeds a threshold voltage $V_T$. The output from comparator 16 is provided to a decade counter 18 which counts the number of pulses applied thereto during the time a control signal so permits. The control signal may be provided from means (not shown) during the time that the volume of blood having cells counted is passed through the flow cell opening. After the control signal indicates the counting is complete, the count in decade counter 18 indicates the number of red blood cells counted for the precise volume of blood being measured.

Analyzer 10 also includes a hemoglobin detector 20 which provides an analog voltage HGB manifesting the value of the hemoglobin of the sample of blood being tested. This voltage is provided by a photocell used in making the colormetric measurement at a certain wavelength of a solution of the blood and other chemicals in a manner well known in the art. Detector 20 may also include amplification and scaling means for providing the HGB signal at a proper magnitude.

The B signal from comparator 16 is also applied to a binary counter 22 which counts the number of B pulses during the time the control signal applied to counter 22 so allows. The binary count in counter 22 is applied to a digital-to-analog converter 24, which converts the digital count manifested at the output of counter 22 into an analog voltage RBC manifesting the number of red blood cells detected and counted.

To determine the hematocrit value, the A signal at the output of amplifier 14 is provided to a differentiating circuit 26, which provides the signal shown as waveform C in FIG. 2. Waveform C has, for each cell pulse, a leading positive pulse and trailing negative pulse and a zero crossing between the two pulses which occurs at the time of maximum amplitude of the A signal pulses. The output from the differentiating circuit 26 is applied to a zero cross detector circuit 28 which provides waveform D shown in FIG. 2. Waveform D is a narrow trigger pulse signal applied each time the amplitude of the differentiated C signal crosses zero. The output from zero cross detector circuit 28 is applied to the set input to trigger monostable multivibrator 30 if the B pulse applied to the inhibit input thereof is occurring. Multivibrator 30 provides the E signal shown in FIG. 2, that is, a fixed duration pulse of, for instance, three microseconds. The E signal is applied to the gate of field effect transistor 32 to render it conductive.

The A signal from amplifier 14 is connected to one main electrode of field effect transistor 32, the other main electrode of which is connected to integrator 34. When multivibrator 30 is triggered, thereby rendering transistor 32 conductive, waveform F is provided to integrator circuit 34.

Waveform F has approximately straight line sides, an upper portion equal to the magnitude of waveform A and a duration equal to the duration of the monostable multivibrator 30 output pulse. Integrator circuit 34 integrates each of the F pulses applied thereto, and provides an analog voltage signal HCT, shown as waveform G in FIG. 2, which is equal to the integral of the F waveform. This voltage is proportional to the hematocrit value.

Figure 3:
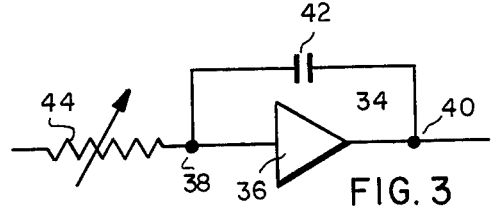
FIG. 3 shows a circuit diagram of the integrator shown in FIG. 1.

Referring now to FIG. 3, a circuit diagram of integrator 34 is shown and includes an operational amplifier 36 having an input 38 and an output 40. Connected between input 38 and output 40 is a capacitor 42 and connected between transistor 32 and input 38 is a variable resistor 44. The value of capacitor 42 and the value set for resistor 44 scales the voltage provided by integrator 34 and these values are selected to cause the voltage at output 40 to manifest the hematocrit value. In use resistor 44 may be adjusted by the operator during a calibrating mode of operation when a sample having a known hematocrit value is used.

In addition, analyzer 10 includes an analog-to-digital converter 46 having a data input and reference input. Analog signals are provided to both the data input and the reference input and a digital output signal appears at the output indicated schematically by five output digital lines. The digital value manifested by the output signal from converter 46 is equal to the analog signal applied to the data input divided by the analog signal applied to the reference input.

To couple the proper signals to the analog-to-digital converter 46, a double ganged rotary switch 48 is provided. Rotary switch 48 has two output terminals 50 and 52 and two sets of five input terminals correspondingly associated with each output terminal and respectively designated as HGB, HCT, MCHC, MCH, and MCV. A switching arm connected to each output terminal selectively connects the same corresponding one of the two sets of input terminals to that output terminal so that the following respectively ordered determinations are made: Hemoglobin, hematocrit, mean corpuscular hemoglobin, mean corpuscular hemoglobin concentration and mean corpuscular volume. The HGB signal is connected to the HGB, MCHC and MCH input terminals associated with output terminal 50. The RBC signal is connected to the MCH and MCV input terminals associated with output terminal 52. The HCT signal is connected to the HCT and MCV input teminals associated with the output terminal 50 and to the MCHC input terminal associated with output terminal 52. A reference direct current voltage of, for instance, 5 volts, is connected to the HGB and HCT input terminals associated with output terminal 52.

Connected in this manner, when the two switching arms connect the HGB input terminals to the output terminals 50 and 52, the value manifested at the output of analog-to-digital converter 46 is the hemoglobin value. When the switching arms connect the HCT input terminals to the output terminals 50 and 52, the value manifested at the output of converter 46 is the hematocrit value. When the switching arms connect the MCHC input terminals to the output terminals 50 and 52, the value manifested at the output of converter 46 is the mean corpuscular hemoglobin concentration value. When the switching arms connect the MCH input terminals to the output terminals 50 and 52, the signal manifested at the output of converter 46 is the mean corpuscular hemoglobin. Finally, when the switching arms connect the MCV input terminals to the output terminals 50 and 52, the signal manifested at the output of converter 46 is the mean corpuscular volume.

The digital outputs from converter 46 and counter 18 are applied to a digital display 54 which provides a numerical display manifesting the digital numbers applied thereto. Display 54 may be under the control of signals (not shown) causing it to display the desired signals upon command of the operator.

What is claimed is:

1. In a blood cell analyzer in which a cell signal is provided in response to the detection of blood cells in a precise volume of blood, said cell signal including a plurality of pulses, with each pulse representing the detection of one cell and with the magnitude of each pulse relating to the size of each detected cells, hematocrit measuring means for providing a voltage relating to the hematocrit of the blood comprising:

integration means for summing signals applied thereto;
controlled switching means for coupling said pulses to integration means; and
detecting means for detecting the maximum of magnitude of each pulse of said cell signal and for producing a gate signal indicative of said detected maximum magnitude and having a fixed, preselected width which is narrow compared to a typical pulse width, said detecting means being coupled to said controlled switching means for rendering said controlled switching means conductive in response to said gate signal, whereby said integrator is incremented by a voltage indicative of a peak portion of each pulse and the voltage stored in said integration means at the completion of said cell signal comprises the voltage relating to the hematocrit of the blood.

2. The hematocrit measuring means according to claim 1 wherein said detecting means comprises a differentiating circuit providing a differential signal and means connected to said differentiating circuit for producing said gate signal when said differential signal reaches a preselected value.

3. The hematocrit measuring means according to claim 2 wherein said means for producing said gate signal comprises a zero crossing detector and a monostable multivibrator connected for triggering by a trigger signal from said zero crossing detector, the output of said multivibrator comprising said gate signal.

4. The hematocrit measuring means according to claim 2 further comprising means for inhibiting said multivibrator when said pulse is below a preselected threshold level.

5. The hematrocrit measuring means according to claim 4 further comprising means for comparing the voltage stored in said integration means at the completion of said cell signal to a reference voltage and converting the result of said comparison to a digital hematocrit indication.

* * * * *